United States Patent [19]

Kornfeld et al.

[11] 4,166,182
[45] Aug. 28, 1979

[54] 6-N-PROPYL-8-METHOXYMETHYL OR METHYLMERCAPTOMETHYLERGOLINES AND RELATED COMPOUNDS

[75] Inventors: Edmund C. Kornfeld; Nicholas J. Bach, both of Indianapolis, Ind.

[73] Assignee: Eli Lilly and Company, Indianapolis, Ind.

[21] Appl. No.: 875,978

[22] Filed: Feb. 8, 1978

[51] Int. Cl.$^2$ .................... C07D 457/02; A61K 31/48
[52] U.S. Cl. ........................................ 546/67; 424/261
[58] Field of Search ........................ 260/285.5; 546/67

[56] References Cited

U.S. PATENT DOCUMENTS

| | | | |
|---|---|---|---|
| 3,901,894 | 8/1975 | Kornfeld et al. | 260/285.5 |
| 3,920,664 | 11/1975 | Clemens et al. | 260/285.5 |
| 3,959,288 | 5/1976 | Bach et al. | 260/285.5 |
| 4,054,660 | 10/1977 | Clemens et al. | 260/285.5 |

OTHER PUBLICATIONS

Hashimoto et al.; Eur. J. Pharmacol.; vol. 45, pp. 341–348, (1977).
Hofmann, Die Mutter Kornalkaloide, pp. 66–67, (1964).
Cassady et al,, Lloydia, vol. 40, pp. 90–96, (1977).
Bernardi et al., Il Farmaco-Ed. Sc., vol. 30, pp. 789–801, (1975).
Krepelka et al., Coll. Czech. Chim. Comm., 42, pp. 1209–1215, (1976).
Fehr et al., Helv. Chim. Acta, vol. 53, pp. 2194–2201, (1970).
Niwaguchi et al.; J. Pharm. Soc. (Japan), pp. 673–677, (1975).
Lieberman et al.; Neurology, vol. 25, pp. 459–462, (1975).
Calne et al., British Med. Jour. 4, pp. 442–444, (1974).
Coward et al.; Pschopharmacology 52, pp. 165–171, (1977).
Greenacre et al.; Br. J. Clin. Pharmac., 3, pp. 571–574, (1976).
Shaw et al., The Lancet, p. 194, (1976).

Primary Examiner—Donald G. Daus
Assistant Examiner—Mary C. Lee
Attorney, Agent, or Firm—James L. Rowe; Arthur R. Whale

[57] ABSTRACT

6-n-Propyl (ethyl or allyl)-8β-methoxy-(methylsulfinyl, methylsulfonyl, or methylmercapto) methylergolines, 8-ergolenes or 9-ergolenes, useful as prolactin inhibitors and in the treatment of Parkinsonism.

8 Claims, No Drawings

6-N-PROPYL-8-METHOXYMETHYL OR METHYLMERCAPTOMETHYLERGOLINES AND RELATED COMPOUNDS

BACKGROUND OF THE INVENTION

Compounds based on the ergoline ring system:

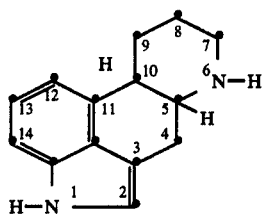

I have a surprising variety of pharmaceutical activities. For example, many of the amides of lysergic acid, which is 8β-carboxyl-6-methyl-9-ergolene, have valuable and unique pharmacologic properties. (The trivial name "ergoline" is given to the above structure and the 9,10 double bonded compound-related to lysergic acid is called a 9-ergolene rather than a 9,10-didehydroergoline. The name D-ergoline or D-8-ergolene or D-9-ergolene is used herein in naming specific compounds. The letter "D" indicates that the C-5 carbon atom configuration has the absolute stereochemistry designated as R and that the hydrogen is β — above the plane of the ring system. However, modern usage has tended to omit the "D", on the ground that the newly synthesized ergolines or ergolenes are universally derivatives of natural products such as lysergic acid or elymoclavine, all of which have R stereochemical — "D" series — configuration and in which the stereochemical integrity at C-5 is maintained. It should be understood that all of the compounds or classes of ergolines or ergolenes disclosed herein also have the R stereochemical configuration, whether or not the specific or generic name is preceded by a "D".) Among these pharmacologically active amides of lysergic acid are included naturally occurring oxytoxic alkaloids — ergocornine, ergokryptine, ergonovine, ergocristine, ergosine, ergotamine, etc. — and synthetic oxytocics such as methergine as well as the synthetic hallucinogen — lysergic acid diethylamide or LSD. The amides of 6-methyl-8-carboxyergoline, known generically as dihydroergot alkaloids, are oxytocic agents of lower potency and also lower toxicity than the ergot alkaloids themselves. Recently, it has been found by Clemens, Semonsky, Meites, and their various coworkers that many ergot-related drugs have activity as prolactin inhibitors. Ergocornine, dihydroergocornine, 2-bromo-α-Ergokryptine and D-6-methyl-8-cyanomethylergoline are examples of such drugs. References embodying some of the newer findings in the field of ergoline chemistry include the following. Nagasawa and Meites, *Proc. Soc. Exp't'l. Biol. Med.*, 135, 469 (1970); Lutterbeck et al., *Brit. Med. J.*, 228, (July 24, 1971); Heuson et al., *Europ. J. Cancer*, 353 (1970); *Coll. Czech. Chem. Commun.*, 33, 577 (1968); *Nature*, 221, 66 (1969); Seda et al., *J. Reprod. Fert.*, 24, 263 (1971); Mantle and Finn, id, 441; Semonsky and co-workers, *Coll. Czech. Chem. Comm.*, 36, 2200 (1971); Schaar and Clemens, *Endocr.*, 90, 285-8 (1972); Clemens and Schaar, *Proc. Soc. Exp. Biol. Med.*, 139, 659–662 (1972), Bach and Kornfeld, *Tetrahedron Letters*, 3225 (1974) and Sweeney, Clemens, Kornfeld and Poore, 64th Annual Meeting, American Association for Cancer Research, April 1973. Recently issued patents in the field of ergolines or of lysergic acid derivatives include the following: U.S. Pat. No. 3,923,812, U.S. Pat. No. 3,929,796, U.S. Pat. No. 3,944,582, U.S. Pat. No. 3,934,772, U.S. Pat. No. 3,954,988, U.S. Pat. No. 3,957,785, U.S. Pat. No. 3,959,288, U.S. Pat. No. 3,966,739, U.S. Pat. No. 3,968,111, U.S. Pat. No. 4,001,242. Many other related and older patents can be found in Patent Office Classification Files 260-256.4 and 260-285.5.

Parkinson's disease, also known as paralysis agitans or shaking palsy, was first described in the late 18th century. It is characterized by tremor, muscular rigidity and loss of postural reflexes. The disease usually progresses slowly with intervals of 10 to 20 years elapsing before the symptoms cause incapacity. The terms "Parkinsonism" and "the Parkinsonian syndrome" include not only Parkinson's disease but also drug-induced Parkinsonism and post-encephalitic Parkinsonism. Treatment of Parkinsonism involves symptomatic, supportive and palliative therapy. Parkinson's disease has been treated with various anticholinergic agents, which agents have a greater beneficial effect on rigidity and akinesia than on tremor. More recently 1-dopa (1-dihydroxyphenylalanine) has been used because of the finding that there is an altered catecholamine content in the brains of patients afflicted with Parkinsonism. Unfortunately, 1-dopa is rapidly metabolized. It has been suggested, therefore, that monoamineoxidase inhibitors be used to retard the degradation of cerebral catechol amines. The use of 1-dopa with a decarboxylase inhibitor was also designed to increase the level of 1-dopa in the brain and hopefully thereby to alleviate the symptoms of Parkinsonism. It has also been suggested (by Corrodi and coworkers) that certain ergot derivatives, such as the naturally occurring alkaloid, ergocornine, are direct dopamine receptor stimulants of long duration and may therefore prove to be of value in the treatment of Parkinson's disease [see *J. Pharm. Pharmac.*, 25, 409 (1973)]. Johnson et al. in *Experientia*, 29, 763 (1973) discuss the evidence of Corrodi et al. that ergocornine and 2-bromo-α-ergokryptine stimulate dopamine receptors and extended their observations to other ergot alkaloids. Trever W. Stone writing in *Brain Research*, 72, 1977 (1974) verified the above experiments and produced further evidence that ergot alkaloids have a dopamine receptor stimulating action.

RELEVANT PRIOR ART

A majority of the chemical modification work carried out in the field of the ergot alkaloids has involved the preparation of synthetic amides of lysergic acid having some, but not all, of the properties of one or more of the naturally-occurring alkaloids. Even with the more recent research devoted to finding prolactin inhibitors without CNS effects, chemical interest has centered on derivatizing the 8-position of the ergoline ring system. However, there are several publications describing the replacement of the 6-methyl group in an ergoline with other groups, particularly higher alkyl groups. Fehr, Stadler and Hoffman, *Helv. Chim. Acta*, 53, 2197 (1970) reacted lysergic acid and dihydrolysergic acid methylesters with cyanogen bromide. Treatment of the resulting 6-cyano derivative with zinc dust and acetic acid yielded the corresponding 6-norderivative, alkylation of which with ethyl iodide, for example, produced a mixture of 6-nor-6-ethyllysergic acid methyl ester and the corresponding isolysergic acid ester 6-Ethyl-8β-methoxycarbonylergoline (the 6-ethyl-9,10 dihydro derivative of methyl lysergate) was also prepared. No utility was given for either of these new derivatives. Bernardi, et al. *Il Farmaco-Ed. Sci.*, 30, 789 (1975) prepared several analogues of the alpha blocker, nicergoline, Starting materials included such compounds as 1-methyl-6-ethyl (allyl, cyclopropylmethyl)-8β-hydroxymethyl-10α-methoxyergoline. These starting materials were in turn converted to the corresponding 10α-methoxy-8β-(5-bromonicotinylmethyl) derivatives. In a recent paper, Krepelka, Army, Kotva and Semonsky, *Coll. Czech. Chem. Commun.*, 42, 1209 (1977) prepared 6-alkyl analogues of 8β-cyanomethylergoline and of 8β-methylergoline (6-norfestuclavine) including the 6-ethyl, 6-n-propyl, 6-isopropyl, 6-n-butyl, 6-isobutyl and 6-n-heptyl derivatives. These compounds increased "antilactation and antinidation" effects in rats by "an order of magnitude" as compared with the corresponding 6-methyl derivatives. Details of such biological testing was to be forthcoming, according to the authors. Cassady and Floss, *Lloydia*, 40, 90 (1977) reported the preparation of 6-alkyl derivatives of elymoclavine (6-methyl-8-hydroxymethyl-8-ergolene). According to their published figures, prolactin inhibitory effects increased on increasing the size of the alkyl group at N-6 from methyl to propyl but fell off with a butyl substituent. Niwaguchi, et al., *J. Pharm. Soc. (Japan) (Yakugaku Zasshi)* 96, 673 (1976) prepared 6-norlysergic acid diethylamide and realkylated this intermediate to prepare the corresponding 6-allyl, 6-ethyl and 6-n-propyl derivatives of LSD. Their pharmacology is discussed in Hashimoto et al., *Europ. J. Pharm.*, 45, 341 (1977).

U.S. Pat. No. 3,920,664 discloses D-2-halo-6-alkyl (Methyl, ethyl, n-propyl)-8β-cyanomethylergolines prepared by demethylating the corresponding 6-methyl compound and realkylating as taught by the procedure of Fehr et al. (supra). U.S. Pat. No. 3,901,894 discloses 6-methyl-8β-methylmercaptomethylergolines optionally substituted at C-2 by chlorine or bromine. U.S. Pat. No. 3,959,288 discloses the analogous 8-methoxymethyl compounds.

Most of the above ergolines or ergolenes are active prolactin inhibitors. Some of these compounds have also proved to be useful in the treatment of Parkinsonism; i.e. α-bromoergokryptine (bromocriptine)-*Brit. J. Clin. Pharm.*, 3, 571 (1976), *Brit. Med. J.*, 4, (1974) page 442 and lergotrile-*Neurology*, 25, 459 (1975).

DESCRIPTION OF THE INVENTION

This invention provides a group of extremely potent prolactin inhibitors and drugs for treating Parkinsonism belonging to the ergoline series and having the following structure:

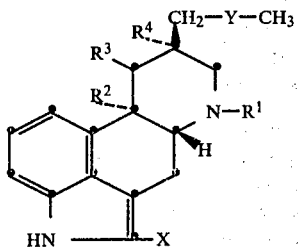

wherein Y is O, SO, $SO_2$ or S, $R^1$ is ethyl, n-propyl, or allyl, X is H, Cl or BR and $R_2$, $R^3$ and $R^4$ when taken singly are hydrogen, and $R^2$ and $R^3$, and $R^3$ and $R^4$, when taken together with the carbon atoms to which they are attached, form a double bond, and pharmaceutically-acceptable acid addition salts thereof.

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-diode, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, napthalene-1-sulfonate, naphthalene-2-sulfonate and the like salts.

Illustrative compounds coming within the scope of this invention include:

D-6-ethyl-8β-methylmercaptomethylergoline maleate

D-2-chloro-6-n-propyl-8β-methoxymethylergoline succinate

D-6-allyl-8β-methylmercaptomethylergoline hydrochloride

D-2-bromo-6-allyl-8β-methoxymethylergoline tartrate

D-6-n-propyl-8β-methylmercaptomethyl-9-ergolene hydrobromide

D-6-n-propyl-8-methoxymethyl-8-ergolene maleate

D-2-chloro-6-allyl-8β-methoxymethyl-9-ergolene benzoate

D-2-bromo-6-ethyl-8-methylmercaptomethyl-8-ergolene phosphate

D-6-ethyl-8β-methylsulfinylmethylergoline

D-6-n-propyl-8β-methylsulfonylmethyl-9-ergolene maleate

D-6-n-propyl-8-methylsulfinylmethyl-8-ergolene tartrate

D-2-chloro-6-allyl-8β-methylsulfinylergoline succinate

D-2-bromo-6-allyl-8β-methylsulfinyl-9-ergolene

A preferred group of compounds are those according to Formula II in which $R^1$ is n-propyl, Y is S and $R^2$, $R^3$, $R^4$ and X have the same meaning as before. A particularly preferred group are those in which $R^1$ is n-propyl, Y is S, X is H and $R^2$, $R^3$, and $R^4$ have the meaning previously assigned. Another preferred group of compounds are those with sulfur-containing groups at C-8; i.e., those in which Y is S, SO or $SO_2$ and in which $R^1$ is n-propyl and $R^2$, $R^3$ and $R^4$ are each hydrogen.

The compounds of this invention can be prepared by various routes from a number of different starting materials. One readily available starting material is lysergic acid (D-6-methyl-8β-carboxy-9-ergolene) produced by fermentation of selected *Claviceps* species. Esterification of the carboxyl at C-8 followed by reduction of the thus-formed ester group yields an 8-hydroxymethyl group. This same compound can be produced from elymoclavine, another starting material available from fermentation by the process of U.S. Pat. No. 3,709,891.

The 6-methyl group of D-6-methyl-8β-hydroxymethyl-9-ergolene produced from either starting material can be removed and replaced by an ethyl, an allyl, or an n-propyl group according to the procedure of U.S. Pat. No. 3,920,664, Example 8. According to this procedure, cyanogen bromide alone, or preferably in an inert solvent, is reacted with, for example, D-6-methyl-8β-hydroxymethyl-9-ergolene to yield the corresponding 6-cyano derivative. Suitable inert solvents for this reaction include chlorinated hydrocarbons such as chloroform, methylenedichloride, carbon tetrachloride, and ethylenedichloride; aromatic hydrocarbons including benzene, toluene or xylene; and polar solvents such as DMA, DMF, and DMSO. The reaction temperature is not critical and temperatures from ambient temperature to the boiling point of the solvent used may be employed. The cyanide group is readily removed as by reduction with zinc dust in acetic acid, thus producing a secondary amine function at N-6, which amine can be alkylated with, for example, ethyl iodide in the presence of base, to yield D-6-ethyl-8β-hydroxymethyl-9-ergolene. The zinc-acetic acid cleavage reaction is usually carried out near the boiling point of the solvent: 100–120° C. Cleavage of the cyano group can also be accomplished by acidic or basic hydrolysis. In addition, other reducing agents can be employed in place of zinc and acetic acid such as Raney nickel and hydrogen. Alternatively, the N-methyl group can be removed from a 9-eroglene by reaction with a chloroformate such as methyl chloroformate, phenyl chloroformate, benzyl chloroformate, trichloroethyl chloroformate and the like to form an intermediary carbamate which can be cleaved to yield the desired 6-nor secondary amine. Alkylation of the secondary amine with an ethyl, n-propyl or allyl halide, tosylate, etc. is carried out in an inert solvent, preferably a polar solvent such as DMA, DMF, acetonitrile, nitromethane, and the like at temperatures in the range 20°–50° C. Suitable bases which may be present in the reaction mixture as acid scavengers include insoluble inorganic bases such as sodium carbonate, potassium carbonate, sodium bicarbonate, sodium hydroxide, and the like, as well as soluble bases such as the tertiary amines, particularly the aromatic tertiary amines like pyridine. Next, the hydroxymethyl at C-8 is esterified with a readily replaceable group such as the p-toluenesulfonyloxy group or the methanesulfonyloxy group (p-tosyl or mesyl derivatives). The esterification reaction utilizes an acid halide or anhydride; i.e., mesylchloride, p-tosyl bromide and the like. The reaction is carried out preferably in an aromatic tertiary amine solvent such as collidine, pyridine, picoline, etc. The reaction temperature is in the range 20°–50° C. This ester group can, in turn, be replaced with a methylmercapto group according to the procedure of U.S. Pat. No. 3,901,894, Example 3. Similarly, the mesyloxy or p-tosyloxy group can be replaced with a methoxy group by reaction with methanol in base or with a methylsulfonyl group by reaction with sodium methanesulfinate. This replacement reaction can be carried out by forming a sodium salt; i.e., sodium methylmercaptide, using a base such as NaH, KH, sodium methoxide or sodium ethoxide. A mutual inert polar solvent is employed such as DMA, DMF, or DMSO. The reaction mixture is usually heated to a temperature in the range 50°–100° C. Replacement of the mesyloxy or p-tosyloxy group by a methoxy group is usually carried out with methanol in the presence of a quaternary ammonium base.

9Ergolenes having an 8-methylsulfinylmethyl group are prepared from the corresponding 8-methylmercaptomethyl compound by reaction with periodate or like oxidizing agent at ambient temperature. Customarily, a water soluble salt of the 9-ergolene is used and water is the reaction solvent.

These 6-n-propyl (ethyl or allyl) 8-methoxy, methylsulfinyl, methylsulfonyl or methylmercaptomethyl-9-ergolenes thus prepared are compounds coming within the scope of this invention. These compounds can in turn be chlorinated or brominated at C-2 by the procedure of U.S. Pat. No. 3,920,664 to yield those compounds of this invention in which $R^1$ is Cl or Br and in which there is a $\Delta^9$ double bond. Halogenating agents which can be employed in this procedure include N-chlorosuccinimide, N-chloroacetanilide, N-chlorophthalimide, N-chlorotetrachlorophthalimide, 1-chlorobenzotriazole, N-chloro-2,6-dichloro-4-nitroacetanilide, N-chloro-2,4,6-trichloroacetanilide and sulfuryl chloride, this latter reagent being used either alone or with boron trifluoride etherate. A useful solvent for the halogenation reaction with N-bromosuccinimide is dioxane. With N-chlorosuccinimide and most of the other positive halogen compounds, DMF is used but with $SO_2Cl_2$, solvents such as $CH_2Cl_2$, $CH_3NO_2$, $CH_3CN$ and the like are employed. The reaction is ordinarily carried out at room temperature.

Lysergic acid, one of the starting materials used above, can also be reduced to the corresponding dihydro compound, dihydrolysergic acid, by procedures available in the art as by catalytic hydrogenation using a platinum oxide or other suitable catalyst in an inert mutual solvent, preferably a lower alkanol. Esterification by standard procedures yields methyl dihydrolysergate for example. The methyl group at N-6 can then be removed by reaction with cyanogen bromide as outlined above to yield a secondary amine group. The secondary amine can then be akylated with either ethyl iodide, n-propyl iodide or allyl bromide to yield a compound carrying an ethyl, n-propyl or allyl group at N-6 and a methoxycarbonyl (ester) group at C-8. The secondary amine can alternatively be acylated with acetyl chloride or propionyl chloride to yield the corresponding amine in the presence of a tertiary amine base at ambient temperature. Reduction of the amide group at N-6 and of the ester group at C-8 simultaneously by a metal hydride reducing agent such as lithium aluminum hydride in THF at room temperature yields the corresponding D-6-ethyl (or n-propyl)-8β-hydroxymethylergoline. Similarly, the D-6-ethyl (or n-propyl, or allyl)-8β-methoxycarbonyl compound can be reduced to the corresponding 8β-hydroxymethyl derivative by a metal hydride reducing agent such as $LiAlH_4$ or $NaBH(OCH_3)_3$ in an etheral solvent (diethylether or THF) at room temperature or such as $NaBH_4$ in ethanol at reflux temperature. Esterification of the hydroxy of the 8β-hydroxymethyl) group with methanesulfonyl chloride as above to yield the mesyloxy derivative followed by the reaction of this derivative with a salt of methanol, methanethiol, or methanesulfinic acid yields the compound of this invention in which $R^2$, $R^3$, $R^4$ and X are all H, $R^1$ and Y having the same meaning as hereinabove except when Y is SO, which compounds are prepared by oxidation of the sulfide (Y is S). Each of these derivatives can then be chlorinated or brominated at C-2 by the procedure of U.S. Pat. No. 3,920,664 to yield those compounds according to the above formula in which X is Cl or Br, $R^2$, $R^3$, and $R^4$ are hydrogen and $R^1$ and Y have the same meaning as before. The same reaction conditions are employed as were used for the preparation of the corresponding $\Delta^9$-ergolenes.

The above ergoline compounds can also be prepared from elymoclavine, the other readily available starting material, by reduction of the $\Delta^8$ double bond to yield D-6-methyl-8β-hydroxymethylergoline. The same sequence of reactions—replacement of the methyl at N-6 with an ethyl, n-propyl or allyl group followed by replacement of the hydroxymethyl with a methoxymethyl, methylsulfonylmethyl or methylmercaptomethyl group via the intermediate mesylate ester—can be carried out as before.

Finally, elymoclavine itself can be subjected to the procedures set forth above in the reaction sequence based on methyl lysergate including removing the methyl group at N-6, involving reaction with cyanogen bromide and removal of the 6-cyano group, followed by reaction of the thus formed secondary amine with an alkyl or allyl halide to yield a D-6-ethyl, n-propyl or allyl-8-hydroxymethyl-8-ergolene. In this instance, since the hydroxyl of the hydroxymethyl group is an allylic hydroxyl, replacement with chlorine is an available procedure and the allylic chlorine itself is readily replaced by a methoxy, methylsulfonyl, or methylmercapto group to yield those compounds of this invention in which $R^2$ is hydrogen, $R^3$ and $R^4$ form a double bond and Y and $R^1$ have the same meanings as before except where Y is SO, which compound is again prepared by oxidation of the corresponding sulfide. Although we prefer to use a mixture of triphenylphosphine and $CCl_4$ as the chlorinating agent for the allylic hydroxyl, other chlorinating agents can be used such as HCl, HBr, diethylether hydrochloride, a phosphorus trihalide or $POCl_3$, care being taken with these more powerful agents to use reaction conditions which avoid undesirable by-products. As before, any of the compounds of this invention in which X is Cl or Br can be prepared from the corresponding compound in which X is H as set forth above. This chlorination or bromination at C-2 can take place with other of the above intermediates in which there is, for example, an ester group at C-8 and the ester group itself is later replaced by a methoxymethyl or methylmercaptomethyl group.

The compounds of this invention and their acid addition salts are white crystalline solids readily recrystallizable from organic solvents. Their preparation is illustrated by the following specific examples.

EXAMPLE 1

Preparation of
D-6-n-Propyl-8β-methylmercaptomethylergoline

A solution was prepared from 100 g. of methyl dihydrolysergate and 2.5 l. of methylene dichloride. 100 g. of cyanogen bromide were added and the reaction mixture stoppered and stored at room temperature for about 24–25 hours. Thin-layer chromatography (TLC) of an aliquot of the solution showed 1 major spot with some minor spots. The organic layer, containing methyl 6-cyano-8β-methoxycarbonylergoline formed in the above reaction, was washed successively with aqueous tartaric acid, water and saturated aqueous sodium chloride and was then dried. Evaporation of the solvent in vacuo yielded a residue which, on TLC, showed one major spot less polar than starting material, said spot corresponding to D-6-cyano-8β-methoxycarbonylergoline. The compound thus prepared melted at about 202°–5° C.; weight=98.5 g.

A reaction mixture containing 59.6 g. of D-6-cyano-8β-methoxycarbonylergoline, 300 g. of zinc dust, 2.5 l. of acetic acid and 500 ml. of water was heated under reflux in a nitrogen atmosphere for about 7 hours, and was then allowed to remain at ambient temperature for another 16 hours. The reaction mixture was filtered and the filtrate poured over ice. The resulting aqueous mixture was made basic with 14 N aqueous ammonium hydroxide and the alkaline layer extracted with chloroform. The chloroform layer was separated, washed with saturated aqueous sodium chloride, and then dried. Evaporation of the chloroform yielded a residue comprising D-8β-methoxycarbonylergoline formed in the above reaction; m.p.=154°–6° C.; weight=46.9 g. TLC showed one major spot and a smaller spot corresponding to starting material.

Alternatively, a solution of 98.5 g. of D-6-cyano-8β-methoxycarbonylergoline was hydrogenated with Raney nickel in DMF (dimethylformamide) solution. The initial hydrogen pressure was 50 psi. After completion, the hydrogenation mixture was filtered and the filtrate concentrated in vacuo to a 200 ml. volume. This mixture was poured into aqueous tartaric acid and the acidic layer extracted with ethyl acetate. The acidic aqueous layer was then made basic with 14 N aqueous ammonium hydroxide and the alkaline layer extracted with ethyl acetate. This ethyl acetate layer was separated, washed with water, with saturated aqueous sodium chloride solution and then dried. Evaporation of the solvent in vacuo yielded D-8β-methoxycarbonylergoline melting at 150°–3° C.; yield=68.8 g. (76 percent).

A reaction mixture was prepared from 10.8 g. of D-8β-methoxycarbonylergoline, 10 ml. of n-propyl iodide and 8.2 g. of potassium carbonate in 200 ml. of DMF. The reaction mixture was stirred at room temperature under nitrogen for about 16 hours. TLC indicated one major spot with two minor spots. The reaction mixture was diluted with water and the aqueous layer extracted with ethyl acetate. The ethyl acetate extract was separated, washed with water, with saturated aqueous sodium chloride and then dried. Evaporation of the solvent in vacuo yielded a residue which gave essentially the same TLC pattern as before. The residue was dissolved in chloroform containing 2 percent methanol and filtered through 200 g. of florisil. Evaporation of the solvent in vacuo yielded 8.55 g. of D-6-n-propyl-8β-methoxycarbonylergoline melting at 203°–6° C.

About 720 mg. of D-6-n-propyl-8β-methoxycarbonylergoline were dissolved in 25 ml. of dioxane and 50 ml. of methanol. 1 Gram of sodium borohydride was added and the reaction mixture refluxed under nitrogen for about 2 hours. A second gram of sodium borohydride was added after one hour. TLC showed one major polar spot and a minor spot. The reaction mixture was cooled, diluted with water, and the aqueous mixture extracted with a chloroform-isopropanol solvent mixture. The organic layer was separated, washed with saturated aqueous sodium chloride and dried. Evaporation of the organic solvent yielded a residue consisting of D-6-n-propyl-8β-hydroxymethylergoline which was crystallized from an ether-hexane solvent to yield crystals melting at about 167°–9° C.; yield=620 mg.

A solution was prepared from 31.2 g. of D-6-n-propyl-8β-hydroxymethylergoline and 400 ml. of pyridine. Twenty ml. of methanesulfonyl chloride were added slowly to the pyridine solution. After the addition had been completed, the mixture was stirred for about one hour and was then poured into an ice 14 N ammonium hydroxide mixture. The alkaline aqueous layer was extracted with ethyl acetate. The ethyl acetate layer was separated, was washed with water and with saturated aqueous sodium chloride and was then dried. Evaoration of the organic solvent yielded a residue which, on TLC, consisted of one major spot with several minor spots. The chloroform solution of the residue was chromatographed over 300 g. of florisil using chloroform containing increasing amounts of methanol (from 0 to 4 percent) as the eluant. D-6-n-propyl-8β-mesyloxymethyl-ergoline obtained in purified form from this chromatographic procedure melted at about 178–180° C. with decomposition; weight=25.6 g.

Analysis Calc: C, 62.96; H, 7.23; N, 7.77; S. 8.85. Found: C, 62.66; H, 6.94; N, 7.46; S, 9.04.

Twenty-five grams of methylmercaptan were dissolved inn 200 ml. of dimethyl acetamide (DMA). The solution was cooled in an ice-water bath to about 0° C. Next, 14.4 g. of sodium hydride (as a 50 percent suspension in mineral oil) were added in portions, thus forming the sodium salt of methylmercaptan. The sodium salt suspension was warmed to room temperature. A solution of 10.9 g. of D-6-n-propyl-8β-mesyloxymethylergoline in 60 ml. of DMA were slowly added. The reaction mixture was stirred for one hour under nitrogen and then diluted with water. The aqueous layer was extracted with ethyl acetate and the ethyl acetate layer separated. The separated layer was washed with water and with saturated aqueous sodium chloride and was then dried. Evaporation of the solvent yielded a residue consisting of D-6-n-propyl-8β-methylmercaptomethylergoline formed in the above reaction. The residue showed a single major spot under TLC; weight=6.9 g.; m.p.=206–9° C. with decomposition. The residue was further purified by suspending it in 100 ml. of boiling methanol. 1.6 ml of methanesulfonic acid in 10 ml. of methanol were added to the refluxing solution. After the addition had been completed, the mixture was allowed to cool during which time crystals of D-6-n-propyl-8β-methylmercaptomethylergoline methanesulfonate precipitated. The solution was cooled and then filtered. 6.0 Grams of salt were obtained melting at about 225° C. with decomposition.

Analysis Calc: C, 58.50; H, 7.36; N, 6.82; S, 15.62. Found: C, 58.45; H, 7.39; N, 6.92; S, 15.62.

EXAMPLE 2

Preparation of D-6-n-Propyl-8β-methoxymethylergoline

A reaction mixture was prepared from 8.4 g. of D-6-n-propyl-8β-mesyloxymethylergoline from Example 1, 50 ml. of a 40 percent methanol solution of trimethylbenzylammoniummethylate and 200 ml. of DMA as a solvent. The reaction mixture was refluxed under a nitrogen atmosphere for about 1.25 hours. TLC showed 1 major spot in addition to a starting material spot. The reaction mixture was cooled and diluted with ethyl acetate. The ethyl acetate layer was separated, washed with water and with saturated aqueous sodium chloride and then dried. The solvent was removed by evaporation. 5.00 g. of the residue containing D-6-n-propyl-8β-methoxymethylergoline were obtained. The compound melted at 223–6° C. with decomposition. The methanesulfonate salt was prepared as in Example 1 to yield D-6-n-propyl-8β-methoxymethylergoline methanesulfonate melting at 202–4° C. aftr crystallization from ether-ethanol solvent mixture. Yield=4.09 g.

Analysis Calc: C, 60.89; H, 7.66; N, 7.10; S, 8.13. Found: C, 60.60; H, 7.79; N, 7.18; S, 8.08.

EXAMPLE 3

Preparation of D-6n-Propyl-8β-hydroxymethylergoline

A solution was prepared from 9.25 g. of D-8β-methoxycarbonylergoline and 100 ml. of pyridine. 25 ml. of propionic anhydride were added and the reaction mixture stirred at room temperature for one hour. The reaction mixture was then poured into five percent aqueous ammonium hydroxide and 2 liters of water were added. The subsequent mixture was cooled and filtered. The filter cake contained D-6-propionyl-8β-methoxycarbonylergoline which melted at 260–3° C. with decomposition; weight=9.30 g.

Analysis Calc.: C, 69.92; H, 6.79; N, 8.58 Found: C, 70.14; H, 6.99; N, 8.73.

A suspension of 9.8 g. of D-6-propionyl-8β-methoxycarbonylergoline was prepared in 1000 ml. of THF (tetrahydrofuran). Five grams of lithium aluminum hydride were added in portions while the reaction mixture was cooled in an ice-water bath. After the addition of the lithium aluminum hydride had been completed, the reaction mixture was allowed to warm to ambient temperature. It was then refluxed under a nitrogen atmosphere for about 16 hours. The reaction mixture was then cooled to about 0° C. and any excess lithium aluminum hydride plus other organometallics decomposed by the seriatim addition of ethyl acetate, ethanol and water. The reaction mixture was then diluted with water and the aqueous layer extracted several times with a chloroform-isopropanol solvent mixture. The organic extracts were separated, combined, and the combined extracts washed with saturated aqueous sodium chloride. The organic layer was then dried and the solvent removed by evaporation. The residue, comprising D-6-n-propyl-8β-hydroxymethylergoline formed in the above reduction, was recrystallized from methanol to yield 4.75 g of material melting at 174–6° C. A second recrystallization from methanol yielded D-6-n-propyl-8β-hydroxymethylergoline melting at 176–8° C.

Analysis Calc: C, 76.02; H, 8.51; N, 9.85. Found: C, 75.73; H, 8.33; N, 9.63.

This compound can be transformed via the mesylate ester to the corresponding 8β-methylmercaptomethyl derivative etc.

EXAMPLE 4

Preparation of D-6-Allyl-8β-methylmercaptomethyl ergoline

Two grams of D-8β-methoxycarbonylergoline were dissolved in 75 ml. of DMF. 1.7 g. of potassium carbonate were added followed by 0.71 ml. of allyl bromide. The reaction mixture was stirred at ambient temperature under a nitrogen atmosphere for about 3½ hours. TLC indicated a single major fast-moving spot. The reaction mixture was diluted with water and the resulting aqueous layer extracted with ethyl acetate. The ethyl acetate layer was separated, washed with water, and with saturated aqueous sodium chloride and then dried. Evaporation of the solvent in vacuo yielded a residue which after recrystallization from methanol, yielded 570 mg. of D-6-allyl-8β-methoxycarbonylergoline melting at 146–8° C.

Analysis Calc: C, 73.52; H, 7.14; N, 9.03. Found: C, 73.27; H, 7.24; N, 8.97.

Four and eight-tenths grams of D-6-allyl-8β-methoxycarbonylergoline wre dissolved in a mixture of 50 ml. of dioxane and 100 ml. of methanol. Five grams of sodium borohydride were added and the resulting reaction mixture was heated to refluxing temperature for about 2 hours. A second 2 g. batch of sodium borohydride was added after 1 hour. The reaction mixture was diluted with water and 14 N aqueous ammonium hydroxide. The alkaline aqueous layer was extracted several times with a chloroform-isopropanol solvent mixture. The organic extracts were combined and the combined extracts washed with saturated aqueous sodium chloride and then dried. Evaporation of the solvent yielded a residue comprising D-6-allyl-8β-hydroxymethylergoline. The compound melted at 204–6° C. after recrystallization from a methanol-ether solvent mixture.

Analysis Calc: C, 76.56; H, 7.85; N, 9.92. Found: C, 76.35; H, 7.72; N, 9.65.

A solution was prepared from 3.77 g. of D-6-allyl-8β-hydroxymethylergoline and 100 ml. pyridine. 2.5 ml. of methanesulfonyl chloride were added and the resulting mixture stirred at ambient temperature for about three hours. The reaction mixture was then diluted with water and 14 N aqueous ammonium hydroxide. The aqueous layer was extracted several times with ethyl acetate. The ethyl acetate extracts were combined, the combined extracts washed with water and saturated aqueous sodium chloride and then dried. Evaporation of the solvent yielded D-6-allyl-8β-mesyloxymethylergoline which melted at 195–6° C. with decomposition, after recrystallization from a chloroform-methanol solvent mixture; yield=3.5 g.

Analysis Calc: C, 63.31; H, 6.71; N, 7.77; S, 8.89 Found: C, 63.03; H, 6.49; N, 7.51; S, 8.68.

Following the procedure of Example 1, a sodium salt was prepared from 12 g. of methylmercaptan, an excess of NaH and 150 ml. of DMf. A solution of 4.3 g. of D-6-allyl-8β-mesyloxymethylergoline in 50 ml. of DMF was added rapidly to the sodium methylmercaptide mixture. The reaction mixture was stirred for one hour under a nitrogen atmosphere and was then diluted with water. The aqueous layer was extracted with ethyl acetate. The ethyl acetate layer was separated, washed with water and with saturated aqueous sodium chloride and then dried. Evaporation of the ethyl acetate yielded a residue comprising D-6-allyl-8β-methyl-mercaptomethylergoline formed in the above reduction. The residue was dissolved in chloroform, and the chloroform solution chromatographed over 200 g. of florisil using chloroform containing increasing amounts of methanol (0–2 percent) as the eluant. 3.0 Grams of D-6-allyl-8β-methylmercaptomethylergoline melting at 171–3° C. were obtained. The methanesulfonate salt was prepared as in Example 1, and melted at 272–4° C. with decomposition; yield=3.05 g.

Analysis Calc: C, 58.79; H, 6.91; N, 6.86; S, 15.70. Found: C, 58.63; H, 6.76; N, 6.61; S, 15.71.

EXAMPLE 5

Alternate Preparation of D-6-n-Propyl-8β-methoxycarbonylergoline 1.7 Grams of D-6-allyl-8β-methoxycarbonylergoline prepared by the method of the previous example were dissolved in 40 ml. of THF and hydrogenated over 0.5 g. of 5 percent palladium-on-carbon at ambient temperature with an initial hydrogen pressure of 60 psi. After 23 hours, the hydrogenation was completed and the mixture filtered. The solvent was evaporated from the filtrate in vacuo. The resulting residue gave two spots on TLC, one a new spot and the other corresponding to the 6-nor compound. The residue was dissolved in chloroform and the chloroform solution chromatographed over 30 g. of florisil using chloroform containing increasing amounts of methanol (0 to 4 percent) as the eluant. Fractions containing D-6 -n-propyl-8β-methoxycarbonylergoline as determined by TLC were combined and yielded crystalline material melting at 204°–6° C.; yield=740 mg. Recrystallization from a methanol-chloroform solvent mixture yielded D-6-n-propyl-8β-methoxycarbonyl-ergoline melting at 209°–211° C.; yield=465 mg.

Analysis Calc: C, 73.05; H, 7.74; N, 8.97. Found: C, 72.84; H, 7.49; N, 8.67.

EXAMPLE 6

Preparation of D-6-ethyl-8β-methylmercaptomethylergoline

A solution was prepared from 6.5 g. of D-6-methyl-8β-hydroxymethylergoline (dihydrolysergol) and 250 ml. of DMF. Eight grams of cyanogenbromide were added and the reaction mixture stirred at ambient temperature under a nitrogen atmosphere for about 16 hours. The solvent was removed in vacuo and the residue diluted with water and filtered. The filter cake was washed well with ethanol and ether. D-6-Cyano-8β-hydroxymethylergoline thus prepared melted above 260° C.

4.3 Grams of D-6-cyano-8β-hydroxymethylergoline were added to 100 ml. of 6 N aqueous hydrochloric acid and the resulting acidic reaction mixture refluxed under a mitrogen atmosphere for about 2 hours. Thin-layer chromatography of the acidic mixture indicated no mobile spots. The reaction mixture was poured over ice and then made basic with 14 N aqueous ammonium hydroxide. The filter cake, comprising the secondary amine D-8β-hydroxymethylergoline formed in the above reaction weighed 3.65 g. and was used without further purification.

A solution of 3.65 g. of D-8β-hydroxymethylergoline in 100 ml. of DMF was prepared to which were added 4.1 g. of potassium carbonate. 1.4 g. of ethyl iodide were added and the reaction mixture stirred at ambient temperature under nitrogen for about 23 hours, after which time water was added. The aqueous mixture was extracted with several portions of ethyl acetate, the ethyl acetate extracts were combined and the combined extracts washed with water and with saturated aqueous sodium chloride ans were then dried. Evaporation of the solvent yielded as a residue D-6-ethyl-8β-hydroxymethylergoline formed in the above reaction. The residue was recrystallized from a mixture of chloroform and methanol to give D-6-ethyl-8β-hydroxymethylergoline as single spot material on thin-layer chromatography; weight=1.06 g.

Analysis Calc: C, 75.52; H, 8.20; N, 10.36. Found: C, 75.60; H, 7.93; N, 10.06.

A solution was prepared from 2.7 g. of D-6-ethyl-8β-hydroxymethylergoline and 100 m. of pyridine. 1.5 ml. of mesyl chloride were added and the consequent reaction mixture stirred for one hour. The reaction mixture was then diluted with water and made basic by the addition of 14 N aqueous ammonium hydroxide. The alkaline layer was extracted several times with ethyl acetate and the ethyl acetate extracts combined. The combined extracts were washed with water, with saturated aqueous sodium chloride and then dried. Evaporation of the solvent yielded a residue comprising D-6-ethyl-8β-mesyloxymethylergoline formed in the above reaction. The residue showed one major spot on thin-layer chromatography. The residue was chromatographed over 200 g. of florisil using chloroform containing increasing amounts (0 to 5%) of methanol. The chromatogram was followed by thin-layer chromatography. Fractions shown to contain D-6-ethyl-8β-mesyloxymethylergoline by TLC were combined to yield 1.50 g. of crystalline material melting at 184°–5° C. with decomposition after recrystallization.

Analysis Calc: C, 62.04; H, 6.94; N, 8.04; S, 9.20. Found: C, 62.16; H, 6.73; N, 8.01; S, 9.24.

A solution of 2.9 g. of methylmercaptan in 75 ml. of DMF was cooled in an ice-water mixture. 2.4 g. of sodium hydride as a 50% suspension in mineral oil was added thereto in portions, thus forming the sodium salt of methylmercaptan. The reaction mixture was allowed to warm to room temperature. A solution of 1.8 g. of D-6-ethyl-8β-mesyloxymethylergoline in 25 ml. of DMF was added thereto in dropwise fashion. The subsequent reaction mixture was stirred at room temperature under nitrogen for 1.25 hours and was then diluted with water. The aqueous mixture was extracted with ethyl acetate. The ethyl acetate extract was washed with water and with saturated aqueous sodium chloride and was then dried. Evaporation of the solvent yielded a residue comprising D-6-ethyl-8β-methylmercaptomethylergoline formed in the above reaction. The residue was substantially one spot material by thin-layer chromatography. The residue was recrystallized from a mixture of ether and hexane to yield crystalline D-6-ethyl-8β-methylmercaptomethylergoline melting at 201°–2° C. with decomposition.

The D-6-ethyl-8β-methylmercaptomethylergoline formed in the above reaction was suspended in 30 ml. of methanol. The suspension was heated on a steam bath and 0.33 ml. of methanesulfonic acid were added, thus forming the methanesulfonate salt. The reaction mixture was cooled to room temperature and then diluted with about 50 ml. of ether. D-6-Methyl-8β-methylmercaptomethylergoline methanesulfonate precipitated upon cooling and was collected by filtration; melting point"254°–6° C. with decomposition; yield=1.80 g.

EXAMPLE 7

Preparation of D-6-n-Propyl-8-methylmercaptomethyl-8-ergolene

Eleven grams of elymoclavine were suspended in 200 ml. of DMF. About 11 g. of cyanogen bromide were added and the resulting mixture stirred at room temperature under nitrogen atmosphere for about 16 hours and was then diluted with water. D-6-cyano-8-hydroxymethyl-8-ergolene formed in the above reaction precipitated and was collected by filtration; weight=8.2 g.; m.p.=215°–22° C. with decomposition. The filter cake, without further purification, was mixed with 300 ml. of acetic acid, 60 ml. of water and 41 g. of zinc dust. The resulting mixture was refluxed under a nitrogen atmosphere for about 20 hours. The reaction mixture was then filtered and the filtrate poured over ice. The filtrate was then made strongly basic with 14 N aqueous ammonium hydroxide. The alkaline layer was extracted several times with a mixture of chloroform and isopropanol. The extracts were combined and the combined extracts washed with saturated aqueous sodium chloride and then dried. Removal of the solvent left a residue consisting of D-8-hydroxymethyl-8-ergolene and its acetate ester. Without further purification, the residue was dissolved in 200 ml. of DMF to which was added 6.2 g. of potassium carbonate and 8 ml. of n-propyl iodide. This reaction mixture was stirred under nitrogen for about 6 hours and was then diluted with water. The aqueous layer was extracted several times with ethyl acetate and the ethyl acetate extracts combined and washed with water and with saturated aqueous sodium chloride and then dried. Evaporation of the solvent yielded a residue which was seen to have two major spots by thin-layer chromatography. The residue was dissolved in 100 ml. of methanol and 100 ml. of dioxane. 25 ml. of 2 N aqueous sodium hydroxide were added and the alkaline mixture stirred under nitrogen for 1.25 hours at room temperature. The reaction mixture was then diluted with water and the aqueous layer extracted several times with a chloroform-isopropanol solvent mixture. The organic extracts were combined and the combined extracts washed with saturated aqueous sodium chloride and then dried. Evaporation of the solvent yielded a residue comprising one major spot by TLC. The residue was dissolved in chloroform and the chloroform solution chromatographed over 200 g. of florisil. Chloroform containing increasing amounts (2–5%) methanol was used as the eluant. Fractions shown by TLC to contain D-6-n-propyl-8-hydroxymethyl-8-ergolene were combined. The solvent was evaporated to dryness and the resulting residue crystallized from ether to yield D-6-n-propyl-8-hydroxymethyl-8-ergolene melting at 189°–191° C. with decomposition; weight=2.9 g.

Analysis Calc: C, 76.56, H, 7.85; N, 9.92. Found: C, 76.30; H, 7.85; N, 9.96.

Eight and one-tenth grams of D-6-n-propyl-8-hydroxymethyl-8-ergolene were suspended in 1000 ml. of acetonitrile containing 39.3 g. of triphenylphosphine and 14.4 ml. of carbon tetrachloride — for this reagent see *Tetrahedron*, 23, 2789 (1967). The consequent reaction mixture was stirred at room temperature under a nitrogen atmosphere for 19 hours. Volatile constituents were then removed in vacuo and the residue diluted with aqueous tartaric acid. The acidic aqueous layer was extracted several times with toluene and the toluene extracts discarded. The aqueous layer then made basic with sodium bicarbonate and the alkaline layer extracted several times with a mixture of chloroform and isopropanol. The organic extracts were separated, and the separated extracts washed with saturated aqueous sodium chloride and then dried. Evaporation of the solvent yielded a residue which showed one major spot on TLC. A solutuion of the residue in a mixture of chloroform and methanol (2%) was chromatographed over 200 g. of florisil. Fractions shown to contain D-6-n-propyl-8-chloromethyl-8-ergolene formed in the above reaction as shown by TLC were combined and the solvent removed therefrom in vacuo. Recrystallization of the resulting residue from a mixture of chloroform and methanol yielded D-6-n-propyl-8-chloromethyl-8-ergolene which decomposed at about 185° C.; weight=4.65 g.; second fraction=2.30 g.

Analysis Calc: C, 71.87; H, 7.04; N, 9.31. Found: C, 71.62; H, 6.89; N, 9.57.

Fifty milliliters of a solution of 25 g. of methylmercaptan in 100 ml. of DMA was diluted with 200 ml. of DMA and the resulting solution cooled in an ice-water mixture. 10.6 g. of sodium hydride as a 50% suspension in mineral oil were added thereto in portions. The reaction mixture was allowed to warm to 75° C. at which point a solution of 6.7 g. of D-6-n-propyl-8-chloromethyl-8-ergolene in 75 ml. of DMA was added rapidly in dropwise fashion. The reaction mixture was stirred for 2 hours at room temperature under nitrogen. The reaction mixture was then cooled, diluted with water, and the aqueous mixture extracted with ethyl acetate. The ethyl acetate solution was separated, washed with water and then saturated aqueous sodium chloride and then dried. Evaporation of the organic solvent left a residue which was substantially one spot material by TLC. A chloroform solution of the residue was chromatographed over 200 g. of florisil using chloroform containing increasing amounts (0 to 3%) of methanol as the eluant. Fractions shown to contain D-6-n-propyl-8-methylmercaptomethyl-8-ergolene by TLC were combined and the organic solvent removed from the combined extracts. Recrystallization of the residue first from ether and then from ethanol yielded 2.70 g. of D-6-n-propyl-8-methylmercaptomethyl-8-ergolene melting at 180°-3° C. with decomposition. Treatment of the residue with maleic acid yielded the maleate salt of D-6-n-propyl-8-methylmercaptomethyl-8-ergolene as an amorphous solid.

Analysis Calc: C, 64.46; H, 6.59; N, 6.54; S, 7.48. Found: C, 64.31; H, 6.51; N, 6.81; S, 7.61.

EXAMPLE 8

Preparation of D-6-n-propyl-8β-methylmercaptomethyl-9-ergolene

Twenty-five grams of methyl lysergate were dissolved in 750 ml. of methylenedichloride. 35 g. of cyanogenbromide were added and the resulting mixture stirred at room temperature under nitrogen for 22 hours. The organic layer was washed with aqueous tartaric acid, water and saturated aqueous sodium chloride. The organic layer was then dried and the organic solvent removed therefrom by evaporation. The resulting residue containing D-6-cyano-8β-methoxycarbonyl-9-ergolene formed in the above reaction showed a single major spot on TLC. The residue was dissolved in 600 ml. of acetic acid and 120 ml. of water to which was added 80 g. of zinc dust. The resulting mixture was heated to reflux temperature under nitrogen for 18½ hours. The reaction mixture was then cooled and filtered. The filtrate was poured over ice and then made basic with 14 N aqueous ammonium hydroxide. The alkaline mixture was extracted several times with chloroform. The chloroform extracts were combined, the combined extracts washed with saturated aqueous sodium chloride and then dried. The product of this reaction methyl-D-6-desmethyllysergate contained some of the corresponding isolysergate. The residue, without further purification, was dissolved in DMF and alkylated with n-propyl iodide and potassium carbonate by the procedure of Example 7 to yield D-6-n-propyl-8β-methoxycarbonyl-9-ergolene containing a small amount of the α-methoxycarbonyl isomer. The residue was suspended in ether and the suspension chromatographed over 150 g. of florisil using ether as the eluant. Those fractions shown to consist mainly of the β-isomer by NMR were combined and the ether removed therefrom by evaporation. The resulting residue was dissolved in ethyl acetate and the organic layer extracted with aqueous tartaric acid. The aqueous extract was separated and then made basic with 14 N aqueous ammonium hydroxide. The now alkaline layer was extracted several times with chloroform, the chloroform extracts were combined, and the combined extracts washed with saturated aqueous sodium chloride and then dried. Evaporation of the chloroform yielded a residue which gave one major spot on TLC. The residue was rechromatographed over 30 g. of florisil using an ether-hexane (1:1) solvent mixture as the eluant. Fractions shown to contain D-6-n-propyl-8β-methoxycarbonyl-9-ergolene by TLC and NMR were combined and reduced with lithium-aluminum hydride as follows: 0.67 grams of residue were dissolved in 75 ml. if THF to which was added in portions 0.5 g. of lithium aluminum hydride. The reaction mixture was stirred at room temperature for 70 minutes and then cooled in an ice-water bath. The organometallics and excess hydride were decomposed by the seriatim addition of ethyl acetate and 10% aqueous sodium hydroxide. The reaction mixture was filtered and the filtrate diluted with water. The aqueous mixture was extracted several times with a chloroform-isopropanol solvent mixture. The organic extracts were combined and the combined extracts washed with saturated aqueous sodium chloride and then dried. Evaporation of the solvent yielded a residue which was shown by TLC to contain three major spots. A chloroform solution of the residue was chromatographed over 30 g. of florisil using chloroform containing increasing amounts (2–10%) of methanol. Four fractions were obtained, each of which was treated separately with 10 ml. of pyridine containing 0.5 ml. of methanesulfonylchloride. Each reaction mixture was diluted with water and then made basic with concentrated ammonium hydroxide. The alkaline solution was in each instance extracted with ethyl acetate and the ethyl acetate extract washed with saturated aqueous sodium chloride and then dried. The fourth of the chromatographic fractions so treated was shown by NMR to consist of D-6-n-propyl-8β-mesyloxymethyl-9-ergolene. The compound was refiltered through florisil to yield 250 mg. of material melting at about 150°C. with decomposition. Next, 1.40 ml. of a solution containing 25 g. of methylmercaptan in 100 ml. of DMA was added to 40 ml. of DMA and the mixture cooled in an ice-water bath. 240 mg. of sodium hydride as a 50% suspension in mineral oil was next added in portions to the cooled solution. The consequent reaction mixture was warmed to about 15° C. A solution of 250 mg. of D-6-n-propyl-8β-mesyloxymethyl-9-ergolene in 10 ml. of DMA was added rapidly in dropwise fashion. The resulting reaction mixture was stirred at room temperture under nitrogen atmosphere for 1.25 hours after which time it was cooled and diluted with water. The resulting aqueous mixture was extracted several times with ethyl acetate. The ethyl acetate layers were separated and combined and the combined layers washed with water and with saturated aqueous sodium chloride. The combined organic layer was dried and the organic solvent was removed by evaporation. The residue was seen to be essentially one spot material on TLC. A solution of the residue in ether was filtered through florisil and the florisil washed with ether. The ether solution was then diluted with hexane to yield crystalline D-6-n-propyl-8β-methylmercaptomethyl-9-ergolene formed in the above reaction. The compound decomposed at about 197° C.; yield=100 mg.

Analysis Calc.: C, 73.03; H, 7.74; N, 8.97; S, 10.26. Found: C, 73.05; H, 7.94; N, 9.26; S, 10.31.

EXAMPLE 9

Preparation of D-2-bromo-6-n-propyl-8β-methyl-mercaptomethylergoline

A solution of 1.62 g. of N-bromosuccinimide in 50 ml. of dioxane was added rapidly in dropwise fashion to a solution of 2.60 g. of D-6-n-propyl-8β-methoxycarbonylergoline line in 100 ml. of dioxane at about 63° C. The reaction mixture was heated for two hours in the range 60°–65° C. under a nitrogen atmosphere. The reaction mixture was then poured over ice and 14 N aqueous ammonium hydroxide. The alkaline mixture was extracted with ethyl acetate and the ethyl acetate extract separated and washed with water and then with saturated aqueous sodium chloride. The ethyl acetate layer was dried and the solvent removed by evaporation. Thin-layer chromatography of the residue showed one major spot. A chloroform solution of the residue containing D-2-bromo-6-n-propyl-8β-methoxycarbonylergoline formed in the above reaction was chromatographed over 35 g. of florisil using chloroform containing 1 percent methanol as the eluant. Fractions shown to contain the major spot material by TLC were combined to yield 1.64 g. of D-2-bromo-6-n-propyl-8β-methoxycarbonylergoline melting at 167°–168° C. Recrystallization from methanol yielded material melting at 168°–169° C.

Analysis Calc.: C, 58.32; H, 5,92; N, 7.16. Found: C, 58.46; H, 5.76; N, 7.20.

A solution of 1.4 g. of D-2-bromo-6-n-propyl-8β-methoxycarbonylergoline in 100ml. of THF was cooled in an ice-water mixture. 1.5 g. of lithium aluminum hydride were added in portions. The reaction mixture was stirred at room temperature for about an hour and then cooled. The excess lithium aluminum hydride and any organometallic substances present were decomposed by the seriatim addition of ethyl acetate and 10 percent aqueous sodium hydroxide. The reaction mixture was further diluted with water, and the aqueous layer extracted with a mixture of chloroform and isopropanol. The organic extract was separated, washed with saturated aqueous sodium chloride, and dried. Evaporation of the chloroform yielded a residue which gave 1 major spot on TLC. Recrystallization of the residue from methanol yielded D-2-bromo-6-n-propyl-8β-hydroxymethylergoline formed in the above reaction; melting point=208°–210° C.; yield=1.19 g.

Analysis Calc.: C, 59.51; H, 6.38; N, 7.71; Br, 21.99. Found: C, 59.55; H, 6.14; N, 7.50; Br, 21.72.

A solution of 1.3 g. of D-2-bromo-6-n-propyl-8β-hydroxymethylergoline was prepared in 50 ml. of pyridine. 1.5 ml. of methanesulfonylchloride were added and the subsequent reaction mixture stirred for 1.5 hours. The reaction mixture was then poured over a mixture of ice and 14 N aqueous ammonium hydroxide. The alkaline aqueous layer was extracted with ethyl acetate and the ethyl acetate layer separated and washed with water and with saturated aqueous sodium chloride. The ethyl acetate solution was dried and the ethyl acetate removed by evaporation. The residue was shown by thin layer chromatography to consist of one major spot. Recrystallization of the residue from methanol yielded D-2-bromo-6-n-propyl-8β-mesyloxymethylergoline; yield=1.43 g.

Analysis Calc.: C, 50.74; H, 6.17; N, 5.92. Found: C, 50.90; H, 6.03; N, 6.00.

Eight milliliters of a solution of methylmercaptan in DMA (40 millimoles of methylmercaptan) and 100 ml. of DMA were cooled in an ice-water bath. 1.6 g. of sodium hydride as a 50 percent suspension in mineral oil was added thereto in portions. The mixture was allowed to warm to about 15° C. at which point a solution of 1.5 g. of D-2-bromo-6-n-propyl-8β-mesyloxymethylergoline in 40 ml. of DMA was added thereto rapidly in dropwise fashion. The consequent reaction mixture was stirred at room temperature under nitrogen for 1.5 hours after which time it was cooled and diluted with water. The aqueous layer was extracted several times with ethyl acetate and the ethyl acetate extracts separated and combined. The combined extracts were washed with water and with saturated aqueous sodium chloride and then dried. Evaporation of the solvent in vacuo yielded a residue consisting of 1 major spot. Recrystallization of the residue from methanol yielded D-2-bromo-6-n-propyl-8β-methylmercaptomethylergoline formed in the above reaction melting at 159°–161° C. (Total yield=1.08 g.).

The methanesulfonate salt was prepared by dissolving 950 mg. of D-2-bromo-6-n-propyl-8β-methylmercaptomethylergoline in about 25 ml. of hot methanol. 0.16 ml. of a methanesulfonic acid solution containing 2.5 millimoles of acid were added and the solution chilled. The reaction mixture was then diluted with ether and 940 mg. of the methanesulfonate salt melting at 256° C. with decomposition were obtained. The starting material for the above reaction, D-6n-propyl-8β-methoxycarbonylergoline can be prepared from methyl dihydrolysergate by the same sequence of reactions as employed in Example 8 to prepare the corresponding 6-n-propyl derivative of methyl lysergate itself.

EXAMPLE 10

Preparation of D-6-n-propyl-8β-methylsulfinylmethylergoline

A solution was prepared by dissolving 1.2 g. of the methanesulfonate salt of D-6-n-propyl-8β-methylmercaptomethylergoline in 100 ml. of water. A solution containing 685 mg. of sodium periodate in 25 ml. of water was added thereto and the resulting reaction mixture stirred at room temperature for 17 hours. The reaction mixture was then diluted with aqueous sodium bicarbonate and the alkaline layer extracted with a mixture of chloroform and isopropanol. The organic extract was separated, washed with saturated aqueous sodium chloride and dried. Evaporation of the solvent yielded a residue which was dissolved in boiling methanol to which 0.2 ml. of methanesulfonic acid had been added. The solution was cooled to room temperature and diluted with an equal volume of ether. The solvents were removed in vacuo and the residue dissolved in 100 ml. of boiling acetone. The acetone solution was filtered and cooled. The crystalline methanesulfonate salt of D-6-n-propyl-8β-methylsulfinylmethylergoline melting at 200°–209° C. with decomposition was obtained.

Analysis Calc.: C, 56.31; H, 7.09; N, 6.57; S, 15.03. Found: C, 56.09; H, 6.85; N, 6.41; S, 14.86.

The corresponding free base was prepared by standard procedures and melted at 173°–175° C. with decomposition.

Analysis Calc.: C, 69.05; H, 7.93; N, 8.48; S, 9.70. Found: C, 68.99; H, 7.68; N, 8.71; S, 9.76

EXAMPLE 11

Preparation of D-6n-propyl-8β-methylsulfonylmethylergoline

A reaction mixture was prepared from 3.6 g. of D-6-n-propyl-8β-mesyloxymethylergoline, 10 g. of sodium methanesulfinate and 200 ml. of DMF. The mixture was heated at 110° C. under nitrogen for 3.75 hours. The reaction mixture was then diluted with water and the aqueous mixture extracted several times with ethyl acetate. The ethyl acetate layers were combined and the combined layers washed with water, with saturated aqueous sodium chloride and were then dried. Evaporation of the ethyl acetate yielded a residue comprising D-6-n-propyl-8β-methylsulfonylmethylergoline formed in the above reaction. The residue was dissolved in chloroform and the chloroform solution chromatographed over 200 g. of fluorosil using chloroform containing increasing amounts (2–4 percent) of methanol as eluant. Two major fractions were obtained, one moving just ahead of starting material on thin-layer chromatography and one moving just behind. Fractions containing this second slower moving component, were combined and the solvent evaporated therefrom. Recrystallization of the residue from methanol yielded crystalline D-6-n-propyl-8β-methylsulfonylmethylergoline melting at 184°–186° C. (total yield = 690 mg.)

Analysis Calc.: C, 65.86; H, 7.56; N, 8.09; S, 9.25. Found: C, 66.08; H, 7.49; N, 7.88; S, 9.05.

The methanesulfonic acid salt was prepared according to standard procedures in methanol.

EXAMPLE 12

Preparation of D-2-chloro-6-n-propyl-8β-methylmercaptomethylergoline 7.2 Grams of D-6-n-propyl-8β-mesyloxymethylergoline were dissolved in 100 ml. of methylene dichloride and 380 ml. of acetonitrile. 6.3 ml. of borontrifluoride etherate were added and the mixture cooled in the range 0°–5° C. Next, over a 10-minute period, a solution of 1.80 ml. of sulfuryl chloride in 30 ml. of methylene dichloride was added in dropwise fashion. The reaction mixture was stirred with cooling for about 30 minutes and then diluted with 5% aqueous ammonium hydroxide. The alkaline layer was extracted several times with a mixture of chloroform and isopropanol. The organic extracts were combined and the combined extracts washed with saturated aqueous sodium chloride and then dried. The solvent was removed by evaporation and the resulting residue dissolved in methylene dichloride. The methylene dichloride solution was chromatographed over 200 g. of florosil using methylene dichloride containing increasing amounts (2–3 percent) of methanol as the eluant. The chromatogram was followed by thin-layer chromatography. Fractions containing a material moving slightly faster than starting material were collected and the solvent evaporated therefrom in vacuo. This fraction containing D-2-chloro-6-n-propyl-8-mesyloxymethylergoline formed in the above reaction was recrystallized from methanol to yield crystalline material melting at 130–131° C. (82 percent yield). A second recrystallization from methanol yielded compound melting at 133°–135° C.

Analysis Calc.: C, 57.49; H, 6.35; N, 7.06; Cl, 8.93; S, 8.08. Found: C, 57.29; H, 6.20; N, 7.12; Cl, 9.13; S, 8.21.

A solution of 7 g. of methylmercaptan in 200 ml. of DMF was cooled in an ice-water bath to about 0° C. 9.6 g. of sodium hydride as a 50 percent suspension in mineral oil was added thereto in portions, thus forming methyl mercaptide. The cooling bath was removed and stirring continued for about 10 minutes at which time, a solution of 6.2 g. of D-2-chloro-6-n-propyl-8β-mesyloxymethylergoline in 75 ml. of DMF was added rapidly in dropwise fashion. The reaction mixture was stirred for an additional hour under nitrogen and then diluted with water. The aqueous solution was extracted several times with ethyl acetate. The ethyl acetate extracts were combined and then combined layers washed with water and then with saturated aqueous sodium chloride. The ethyl acetate layer was dried and the ethyl acetate removed therefrom by evaporation. The residue was washed with ether and the ether wash diluted with hexane. 4.40 g. of crystalline material melting at 183°–186° C. comprising D-2-chloro-6-n-propyl-8β-methylmercaptomethylergoline formed in the above reaction were obtained. The compound was converted to the methane sulfonate salt which melted at 267°–269° C. with decomposition after recrystallization from a methanol-ether solvent.

Analysis Calc.: C, 53.98; H, 6.57; N, 6.29; Cl, 7.97; S, 14.41. Found: C, 54.22; H, 6.64; N, 6.45; Cl, 8.13; S, 14.20.

As evidence of the utility of the compounds of this invention in the treatment of Parkinson's Syndrome, it has been found that they affect turning behavior in a test procedure utilizing 6-hydroxydopamine-lesioned rats. In this test, nigro-neostriatal-lesioned rats are employed, which are prepared by the procedure of Ungerstedt and Arbuthnott, *Brain Res*, 24, 485 (1970). A compound having dopamine agonist activity causes the rats to turn in circles contralateral to the side of the lesion. After a latency period, which varies from compound to compound, the number of turns is counted over a 15-minute period. D-6-n-propyl-8β-methylmercaptomethylergoline mesylate not only had a very short latency period of 6 or 7 minutes but produced an average of 105 turns per lesioned rat.

Results obtained from testing this compound and other related compounds in the rat turning test are set forth in Table 1 below. The compounds were dissolved in water and the aqueous solution injected into the rat by the intraperitoneal route. In the table, column 1 gives the name of the compound, column 2, the IP dose in mg./kg., column 3, percent of test animals exhibiting turning behavior, column 4, latency of effect, column 5, duration of effect, and column 6, average number of turns observed in first 15 minutes after end of latency period.

Table I

| Name of Compound | IP Dose in mg./kg. | % of Rats Exhibiting Turning Behavior | Latency of Effect in Minutes | Duration of Effect in Hours | Average Number of Turns/rat |
|---|---|---|---|---|---|
| D-6-n-propyl-8$\beta$-methylmercapto-methylergoline mesylate | 1 | 100 | 5-7 | 24+ | 105 |
| D-6-ethyl-8$\beta$-methylmercapto-methylergoline mesylate | 1 | 100 | 9 | 2+ | 112 |
| D-6-n-propyl-8$\beta$-methylmercapto-methyl-9-ergolene | 1 | 100 | 4 | 2+ | 200 |
| D-6-n-propyl-8-methylmercapto-methyl-8-ergolene maleate | 1 | 100 | 4 | 1 | 118 |
| D-2-bromo-6-n-propyl-8$\beta$-methyl-mercaptomethylergoline mesylate | 1 | 100 | 5 | 1 | 71 |
| D-6-n-propyl-8$\beta$-methylsulfinyl methylergoline mesylate | 1 | 100 | 7 | 1 | 65 |
| D-6-methyl-8$\beta$-methylmercapto-methylergoline mesylate* | 1 | 50 | 30-45 | ~2 | 51 |
| D-6-n-propyl-8$\beta$-methoxymethyl-ergoline mesylate | 1 | 100 | 6 | 2+ | 111 |

*from U.S. Pat. 3,901,894

The compounds of this invention are also useful as prolactin inhibitors and as such they can be employed in the treatment of inappropriate lactation such as postpartum lactation and galactorrhea. Furthermore the compounds are useful in the treatment of Parkinson's syndrome.

As evidence of their utility in the treatment of diseases in which it is desirable to reduce the prolactin level, the compounds of this invention have been shown to inhibit prolactin according to the following procedure.

Adult male rats of the Sprague-Dawley strain weighing about 200 g. were housed in an air-conditioned room with controlled lighting (lights on 6 a.m.–8 p.m.) and fed lab chow and water *ad libitum*. Each rat received an intraperitoneal injection of 2.0 mg. of reserpine in aqueous suspension 18 hours before administration of the ergoline derivative. The purpose of the reserpine was to keep prolactin levels uniformly elevated. The compounds under test were dissolved in 10 percent ethanol at a concentration of 10 mcg/ml. and were injected intraperitoneally at a standard dose of 50 mcg/kg. Each compound was administered to a group of 10 rats, and a control group of 10 intact males received an equivalent amount of 10 percent ethanol. One hour after treatment all rats were killed by decapitation, and 150 $\mu$l aliquots of serum were assayed for prolactin. The results were evaluated statistically using Student's "t" test to calculate the level of significance, "p", of the changes in prolactin level.

The difference between the prolactin level of the treated rats and prolactin level of the control rats, divided by the prolactin level of the control rats gives the percent inhibition of prolactin secretion attributable to the compounds of this invention. These inhibition percentages are given in Table 2 below. In the table, column 1 gives the name of the compound; column 2, the prolactin level for each group of rats; column 3, the percent prolactin inhibition; and column 4, the level of significance. The data were collected from three separate experiments, each with its own control, and Table 2 sets forth the results obtained by experiment.

Table II

| Name of Compound | Serum Prolactin Level (mg/ml) | Percent Inhibition of Serum Prolactin | Significance Level "P" |
|---|---|---|---|
| Experiment 1 | | | |
| Control | 30.4 ± 3.4 | — | — |
| D-6-n-propyl-8$\beta$-methylmercapto-methylergoline mesylate | 1.6 ± 0.4 | 95% | <0.001 |
| D-6-methyl-8$\beta$-methylmercapto-methylergoline mesylate* | 12.8 ± | 58% | <0.01 |
| Experiment 2 | | | |
| Control | 55.2 ± 4.1 | — | — |
| D-6-n-propyl-8$\beta$-methoxymethyl-ergoline mesylate | 2.4 ± 0.2 | 96% | <0.001 |
| Experiment 3 | | | |
| Control | 42.3 ± 7.3 | — | — |
| D-6-ethyl-8$\beta$-methylmercapto-methylergoline mesylate | 3.9 ± 0.4 | 91% | <0.001 |
| D-6-n-propyl-8$\beta$-methylmercapto-methyl-9-ergolene | 8.1 ± 1.2 | 81% | <0.001 |
| D-6-n-propyl-8-methylmercapto-methyl-8-ergolene maleate | 3.9 ± 0.2 | 91% | <0.001 |
| Control | 42.3 ± 7.3 | — | — |
| D-6-ethyl-8$\beta$-methylmercapto-methylergoline mesylate | 3.9 ± 0.4 | 91% | <0.001 |
| D-6-n-propyl-8$\beta$-methylmercapto-methyl-9-ergolene | 8.1 ± 1.2 | 81% | <0.001 |
| D-6-n-propyl-8-methylmercapto-methyl-8-ergolene maleate | 3.9 ± 0.2 | 91% | <0.001 |
| D-2-bromo-6-n-propyl-8$\beta$-methyl- | | | |

Table II-continued

| Name of Compound | Serum Prolactin Level (mg/ml) | Percent Inhibition of Serum Prolactin | Significance Level "P" |
|---|---|---|---|
| mercaptomethylergoline mesylate | 4.6 ± 0.4 | 89% | <0.001 |
| D-6-n-propyl-8β-methylsulfinyl-methylergoline mesylate | 3.3 ± 0.1 | 92% | <0.001 |

*from U.S. Pat. 3,901,894.

Employing dose response curves, it has been determined that D-6-n-propyl-8β-methylmercaptomethylergoline mesylate is about 100 times more potent as a prolactin inhibitor than is the corresponding D-6-methyl compound and about 30 times more potent in the turning behavior test in 6-hydroxydopamine-lesioned rats than the corresponding D-6-methyl derivative.

In addition, compounds of this invention, particularly D-6-n-propyl-8β-methylmercaptomethylergoline and its Δ[8] and Δ[9] congeners, are extremely potent inhibitors of the high affinity binding of tritiated dopamine to dopamine receptors present in membranes from striatal synaptosomes of bovine brain—see Bymaster and Wong, *Fed. Proc.*, 36, 1006 (1977) and thus likely to be useful in the treatment of Parkinsonism. Table 3 which follows gives a series of determinations of the inhibiting power of several ergolines, 8-ergolenes and 9-ergolenes, both from this invention and from the prior art. In the table, column 1 gives the name of the compound and column 2, $K_i$ (in nanomoles), the concentration of inhibitor required to slow the reaction to one-half of the initial reaction rate.

Table 3

| Name of Compound | $K_i$ (nM) |
|---|---|
| D-6-n-propyl-8β-methylmercapto-methylergoline mesylate | 3 ± 1 |
| D-6-n-propyl-8-methylmercapto-methyl-8-ergolene maleate | 2 |
| D-6-n-propyl-8β-methylmercapto-methyl-9-ergolene | 2 |
| D-2-bromo-6-n-propyl-8β-methyl-mercaptomethylergoline mesylate | 3 |
| D-6-allyl-8β-methylmercapto-methylergoline mesylate | 5 |
| D-6-ethyl-8β-methylmercapto-methylergoline mesylate | ]3.5 |
| D-6-n-propyl-8β-methoxymethyl-ergoline mesylate | 10 |
| Prior Art Compounds | |
| D-6-methyl-8β-methylmercapto-methylergoline mesylate | 13 |
| D-6-methyl-8β-methoxymethyl-ergoline mesylate | 75 |
| D-6-methyl-8β-methylmercapto-methyl-9-ergolene | 6 |
| D-2-chloro-6-methyl-8β-methyl-mercaptomethylergoline mesylate | 6 |

The compounds of this invention, particularly D-6-n-propyl-8β-methylmercaptomethylergoline are, surprisingly, serotonin agonists rather than serotonin antagonists as are most ergolenes or ergolines.

In using the compounds of this invention to inhibit prolactin secretion or to treat Parkinson's syndrome or for other pharmacologic action, an ergoline, 8-ergolene or 9-ergolene according to Formula II above, or a salt thereof with a pharmaceutically-accepted acid, is administered to a subject suffering from Parkinsonism or in need of having their prolactin level reduced in amounts ranging from 0.01 to 3 mg per kg. of mammalian weight. For D-6-n-propyl-8β-methylmercaptomethylergoline, a dose range of 0.01 to 0.5 is used. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, a compound according to Formula II either as the free base or in the form of a salt thereof can also be mixed with standard pharmaceutical excipients and loaded into empty telescoping gelatin capsules or pressed into tablets.

We claim:

1. A compound of the formula

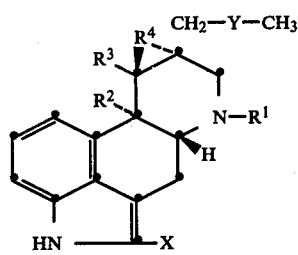

wherein Y is O, SO, SO$_2$ or S, R$^1$ is n-propyl, X is H, Cl or Br and R$^2$, R$^3$ and R$^4$ when taken singly are hydrogen, and R$^2$ and R$^3$, and R$^3$ and R$^4$, when taken together with the carbon atoms to which they are attached, form a double bond, and pharmaceutically-acceptable acid addition salts thereof.

2. A compound according to claim 1 in which Y is S.

3. A compound according to claim 1, said compound being D-6-n-propyl-8β-methylmercaptomethylergoline.

4. A compound according to claim 1, said compound being D-6-n-propyl-8-methylmercaptomethyl-8-ergolene.

5. A compound according to claim 1, said compound being D-6-n-propyl-8β-methylmercaptomethyl-9-ergolene.

6. A compound according to claim 1, said compound being D-6-n-propyl-8β-methylmercaptomethylergoline mesylate.

7. A compound according to claim 1 in which Y is S, X is H and R$^1$ is n-propyl.

8. A compound according to claim 1, said compound being D-6-n-propyl-8β-methoxymethylergoline mesylate.

* * * * *

UNITED STATES PATENT AND TRADEMARK OFFICE

CERTIFICATE EXTENDING PATENT TERM
UNDER 35 U.S.C. 156

Patent No.    : 4,166,182

Dated         : August 28, 1979

Inventor(s)   : EDMUND C. KORNFELD ET AL

Patent Owner  : ELI LILLY AND COMPANY

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 11th day of December 1989.

Jeffrey M. Samuels
Acting Commissioner of
   Patents and Trademarks